US00PP37318P3

(12) United States Plant Patent
Schoone

(10) Patent No.: US PP37,318 P3
(45) Date of Patent: Mar. 10, 2026

(54) ***PHALAENOPSIS* PLANT NAMED 'Amaze'**

(50) Latin Name: *Phalaenopsis hybrida*
Varietal Denomination: Amaze

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/243,676

(22) Filed: Jun. 19, 2025

(65) Prior Publication Data

US 2025/0393486 P1 Dec. 25, 2025

Related U.S. Application Data

(60) Provisional application No. 63/662,415, filed on Jun. 20, 2024.

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP35,584 P3 * 1/2024 Schoone ..... A01H 6/62 Plt./311

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'Amaze', characterized by its upright plant habit; relatively strong flowering stems; healthy and sturdy leaves; freely flowering habit with typically two inflorescences developing per plant, each inflorescence with numerous flowers; flower petals and sepals that are white in color and densely covered with deep purplish red-colored stripes and netting; and good postproduction longevity.

2 Drawing Sheets

Figure 1:
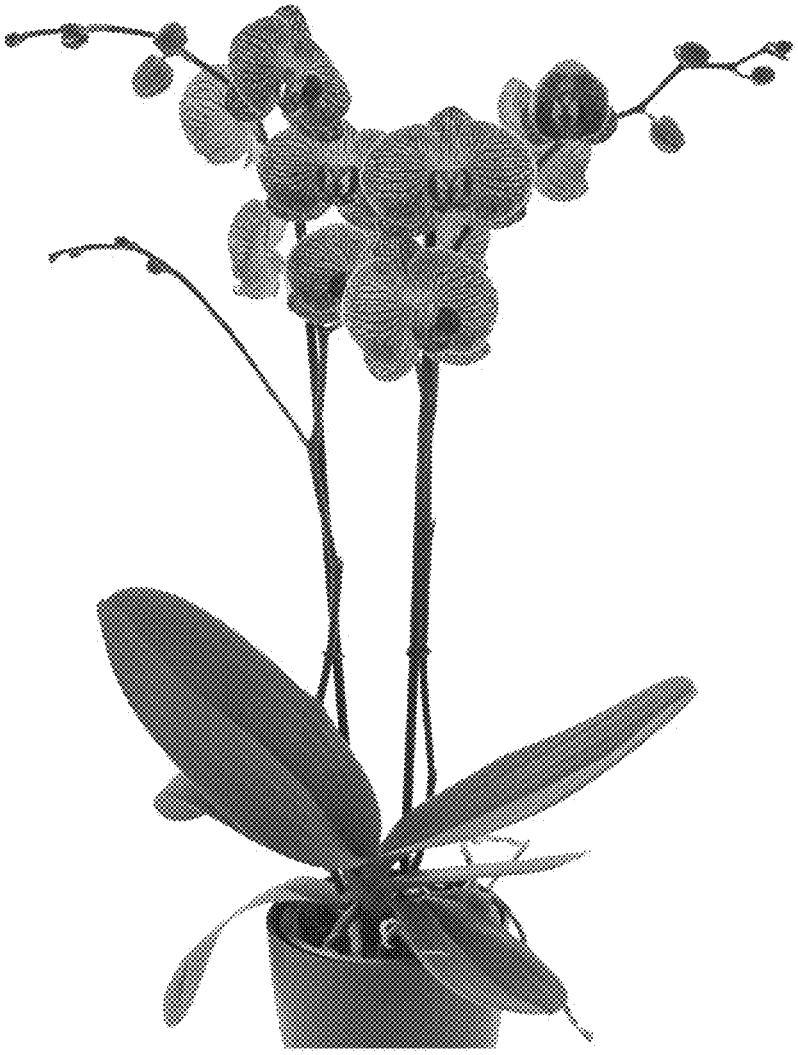

Botanical designation: *Phalaenopsis hybrida.*
Cultivar denomination: 'AMAZE'.

BACKGROUND OF THE INVENTION

The present invention relates to a new and distinct cultivar of *Phalaenopsis* plant, botanically known as *Phalaenopsis hybrida*, and hereinafter referred to by the name 'Amaze'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2014 in Assendelft, The Netherlands of *Phalaenopsis hybrida* 'Mary Stripes', not patented, as the female, or seed, parent with *Phalaenopsis hybrida* 'Arakaki Cherry Stripes', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in June 2020.

Asexual reproduction of the new *Phalaenopsis* plant by in vitro meristem propagation in a controlled environment in Assendelft, The Netherlands since May 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Amaze'. These characteristics in combination distinguish 'Amaze' as a new and distinct *Phalaenopsis* plant:

1. Upright plant habit.
2. Relatively strong flowering stems.
3. Healthy and sturdy leaves.
4. Freely flowering habit with typically two inflorescences developing per plant, each inflorescence with numerous flowers.
5. Flower petals and sepals that are white in color and densely covered with deep purplish red-colored stripes and netting.
6. Good postproduction longevity.

Plants of the new *Phalaenopsis* can be compared to plants of the female parent, 'Mary Stripes'. Plants of the new *Phalaenopsis* differ primarily from plants of 'Mary Stripes' in flower color as the ground color of flowers of plants of the new *Phalaenopsis* is white whereas the ground color of flowers of plants of 'Mary Stripes' is purple. In addition, flowers of plants of the new *Phalaenopsis* are more densely covered in stripes and netting than flowers of plants of 'Mary Stripes'.

Plants of the new *Phalaenopsis* can be compared to plants of the male parent, 'Arakaki Cherry Stripes'. Plants of the new *Phalaenopsis* differ primarily from plants of 'Arakaki Cherry Stripes' in flower color as the ground color of flowers of plants of the new *Phalaenopsis* is white whereas the ground color of flowers of plants of 'Arakaki Cherry Stripes' is purple. In addition, flowers of plants of the new *Phalaenopsis* are more densely covered in stripes and netting than flowers of plants of 'Arakaki Cherry Stripes'.

Plants of the new *Phalaenopsis* can be compared to plants of *Phalaenopsis hybrida* 'Tropic Picotee', not patented. In side-by-side comparisons, plants of the new *Phalaenopsis* differ primarily from plants of 'Tropic Picotee' in the following characteristics:

1. Flowers of plants of the new *Phalaenopsis* are not as broad as flowers of plants of 'Tropic Picotee'.
2. The ground color of the labellum of flowers of plants of the new *Phalaenopsis* is deep purplish red whereas the ground color of the labellum of flowers of plants of 'Tropic Picotee' is white.
3. Flowers of plants of the new *Phalaenopsis* are more densely covered in stripes and netting than flowers of plants of 'Tropic Picotee'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Amaze' grown in a container.

Figure 2:
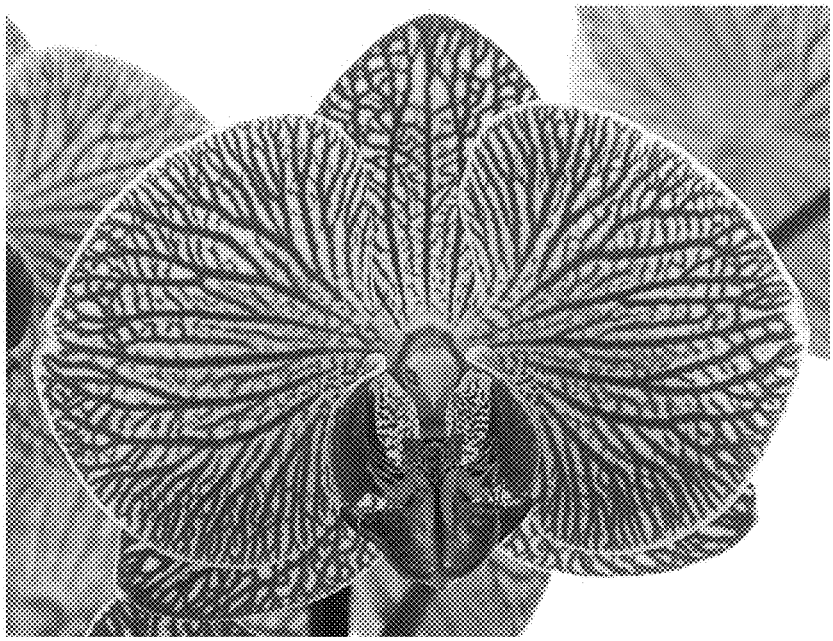

The photograph on the second sheet (FIG. 2) is a close-up view of a typical flower of 'Amaze'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Amaze'.

Parentage:

*Female, or seed, parent.*—*Phalaenopsis hybrida* 'Mary Stripes', not patented.

*Male, or pollen, parent.*—*Phalaenopsis hybrida* 'Arakaki Cherry Stripes', not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; relatively moderately vigorous growth habit and moderate growth rate.

*Plant height, substrate level to top of foliar plane*.—About 21.5 cm.

*Plant height, substrate level to top of floral plane*.—About 47.5 cm.

*Plant diameter or spread*.—About 29.3 cm.

Leaf description:

*Arrangement and quantity*.—Distichous, simple; sessile; about six to seven fully-developed leaves per plant.

*Length*.—About 20.4 cm.

*Width*.—About 7.9 cm.

*Aspect*.—Semi-erect to outwardly arching.

*Shape*.—Obovate to oblong; slightly carinate.

*Apex*.—Unequal broadly acute.

*Base*.—Sheathing. Sheath length: About 2.5 cm. Sheath width: About 1 cm. Sheath color, upper and lower surfaces: Close to a blend of 143B and 143C; marginal edges, close to a blend of 137A and 137B.

*Margin*.—Entire.

*Texture and luster, upper surface*.—Smooth, glabrous; slightly glossy.

*Texture and luster, lower surface*.—Smooth, glabrous; matte.

*Venation pattern*.—Camptodromous.

*Color*.—Developing leaves, upper surface: Close to 137A; towards the base, close to a blend of 137D and 139C with narrow marginal edges, close to 144A. Developing leaves, lower surface: Close to a blend of 138A and 138B; narrow marginal edges, close to 144B. Fully expanded leaves, upper surface: Close to a blend of 143A and 146A; narrow marginal edges, close to 144A; venation, close to 147A. Fully expanded leaves, lower surface: Close to 146B; narrow marginal edges, close to a blend of N144B and N144C; venation, close to 143B.

Inflorescence description:

*Appearance and flowering habit*.—Showy zygomorphic flowers arranged on axillary simple or branched racemes; typically two inflorescences develop per plant; each inflorescence with about 14 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 32.4 cm.

*Inflorescence width*.—About 15.9 cm.

*Flower buds*.—Height: About 2.1 cm. Diameter: About 1.6 cm by 1.8 cm. Shape: Broadly ovate. Color: Close to 195B; surfaces exposed to sunlight are tinged with close to 177D; venation, close to 187D.

*Flower size*.—About 7.9 cm (vertical) by 8.8 cm (horizontal).

*Flower depth*.—About 3.6 cm.

*Petals, quantity and arrangement*.—Three, two lateral petals and one center petal transformed into a labellum.

*Lateral petals*.—Length: About 4.2 cm. Width: About 5.5 cm. Shape: Broadly reniform; not fused. Apex: Obtuse and shallowly retuse. Margin: Entire. Texture and luster, upper and lower surfaces: Smooth, glabrous; velvety; matte. Color: When opening, upper surface: Ground color, close to NN155D; at the base, close to NN78A; primary veins, close to a blend of 71A and 72A; secondary veins, close to 71A and N74A; veins do not extend to the marginal edges. When opening, lower surface: Close to a blend of N155A and 85D; venation, close to NN78A; veins do not extend to the marginal edges. Fully opened, upper surface: Ground color, close to NN155D; at the base, close to NN78A; primary veins, close to a blend of 71A and 72A; secondary veins, close to N74B; veins do not extend to the marginal edges; color does not change with subsequent development. Fully opened, lower surface: Close to a blend of N155A and 85D; venation, close to NN78A; veins do not extend to the marginal edges; color does not change with subsequent development.

*Labella*.—Appearance: Three-parted with two lateral lobes and a central lobe. Length, lateral lobes: About 2.1 cm. Width, lateral lobes: About 1.7 cm. Length, central lobe: About 2.2 cm. Width, central lobe: About 0.8 cm to 2.3 cm. Shape, lateral lobes: Obovate. Shape, central lobe: Ovate-rhomboidal with an elongated apex. Apex, lateral lobes: Obtuse. Apex, central lobe: Broadly acute with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5 mm in length, about 7 mm in width and about 6 mm in height. Color, lateral lobes: When opening and fully opened, upper surface: Close to 71A; towards the apex, close to N155A; at the base, close to NN155A with axial stripes, close to 71A; venation, close to N78A. When opening and fully opened, lower surface: Close to a blend of N155A and 85D; axial stripes and venation, close to 71B, 72A and 72B; lower margin and base tinged with close to 11A. Color, central lobe: When opening, upper surface: Close to 71A and 72A; irregular axial stripes, close to 158A; marginal blotch, close to 7B; at the base, close to 85D with radial stripes, close to 183C; cirrhose apices, close to 71A. When opening, lower surface: Close to NN155A and 71A; towards the margins, close to 72A; towards the apex and venation, close to NN78B; towards the base, close to N78C and N78D; blotches, close to 7B; at the base, close to 156D with blotches, close to N78C and N78D; cirrhose apices, close to 72A. Fully opened, upper surface: Close to 71A, 72A and 72B; irregular axial stripes, close to 11B; marginal blotch, close to 7B; at the base, close to 85D with radial stripes, close to 183C; cirrhose apices, close to 71A. Fully opened, lower surface: Close to NN155A and 71A; towards the margins, close to 72A; towards the apex and venation, close to NN78B; towards the base, close to N78C and N78D; blotches, close to 7A; at the base, close to 156D with blotches, close to N78C and N78D; cirrhose apices, close to 72A. Color, callosities: When developing and fully developed: Close to 4D; marginal edges, close to 6A; towards the apex, close to 15C and 15D; densely dotted and blotched with close to 183C.

*Sepals*.—Quantity and arrangement: Three, one upper dorsal sepal and two lower lateral sepals. Length, dorsal sepal: About 4.2 cm. Width, dorsal sepal: About 3.5 cm. Length, lateral sepals: About 4.3 cm. Width, lateral sepals: About 3 cm. Shape, dorsal sepal: Elliptic. Shape, lateral sepals: Ovate to broadly elliptic. Apex, dorsal sepal: Bluntly acute. Apex, lateral sepals: Narrowly obtuse. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Ground color, close to NN155D; at the base, close to NN78A; primary veins, close to a blend of 71A and 72A; secondary veins, close to 72A and N74A; veins do not extend to the marginal edges. When opening, lower surface: Close to 199D; towards the margins, close to 76C; venation, close to a blend of 71A and 72A. Fully opened, upper surface: Ground color, close to NN155D; at the base, close to NN78A; primary veins, close to a blend of 71A and 72A; secondary veins, close to 72A, 72B, N74A and N74B; veins do not extend to the marginal edges; colors do not change with subsequent development. Fully opened, lower surface: Close to 75B; towards the margins, apex and base, close to 76B; venation, close to 72A; colors do not change with subsequent development. Color, lateral sepals: When opening, upper surface: Ground color, close to NN155D, proximally, tinged with close to 160C; towards the base, close to NN78A; primary veins, close to a blend of 71A and 72A; secondary veins, close to 72A and N74A; veins do not extend to the marginal edges. When opening, lower surface: Close to a blend of 161B and 199D; towards the margins, close to 161C; venation, close to 71A. Fully opened, upper surface: Ground color, close to NN155D, proximally, tinged with close to 160D; at the base, close to NN78A; primary veins, close to a blend of 71A and 72A; secondary veins, close to 72B; veins do not extend to the marginal edges; colors do not change with subsequent development. Fully opened, lower surface: Close to 75B, proximally, tinged with close to 160C; main vein, close to 186B; lateral venation, close to 72A; colors do not change with subsequent development.

*Peduncles*.—Length: About 55.6 cm. Diameter: About 5 mm. Strength: Strong. Aspect: Upright to outwardly arching. Texture and luster: Smooth, glabrous; matte. Color: Close to a blend of N189B and 197A moderately to densely covered with fine dots, close to 147B.

*Pedicels*.—Length: About 3.5 cm. Diameter: About 3 mm. Strength: Moderately strong. Aspect: About 70° from peduncle axis. Texture and luster: Smooth, glabrous; matte. Color: Close to 147D; distal end, close to 75D; proximal end, close to 200C.

*Reproductive organs*.—Androecium: Column length: About 8 mm. Column width: About 6 mm. Column color: Close to N78B; distally, close to NN155D. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to N155A. Ovary length: About 9 mm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Amaze' as herein illustrated and described.

* * * * *